(12) United States Patent
Cerussi et al.

(10) Patent No.: US 9,772,280 B2
(45) Date of Patent: Sep. 26, 2017

(54) PORTABLE BROADBAND DIFFUSE OPTICAL SPECTROSCOPIC IMAGING (DOSI) DEVICE FOR NONINVASIVE TISSUE CHARACTERIZATION

(71) Applicant: The Regents of the University of California, Oakland, CA (US)

(72) Inventors: Albert Cerussi, Rancho Santa Margarita, CA (US); Bruce Tromberg, Irvine, CA (US); Keun-sik No, Irvine, CA (US); Brian Hill, Irvine, CA (US); Pai Chou, Irvine, CA (US)

(73) Assignee: The Regents of the University of California, Oakland, CA (US)

( * ) Notice: Subject to any disclaimer, the term of this patent is extended or adjusted under 35 U.S.C. 154(b) by 153 days.

(21) Appl. No.: 14/760,817

(22) PCT Filed: Jan. 13, 2014

(86) PCT No.: PCT/US2014/011353
§ 371 (c)(1),
(2) Date: Jul. 14, 2015

(87) PCT Pub. No.: WO2014/113333
PCT Pub. Date: Jul. 24, 2014

(65) Prior Publication Data
US 2015/0351635 A1 Dec. 10, 2015

Related U.S. Application Data

(60) Provisional application No. 61/752,702, filed on Jan. 15, 2013.

(51) Int. Cl.
*A61B 6/00* (2006.01)
*G01N 21/47* (2006.01)
(Continued)

(52) U.S. Cl.
CPC ........... *G01N 21/47* (2013.01); *A61B 5/0075* (2013.01); *A61B 5/0084* (2013.01);
(Continued)

(58) Field of Classification Search
CPC ... A61B 5/0075; A61B 5/0084; A61B 5/0091; A61B 5/7225; G01J 3/0264;
(Continued)

(56) References Cited

U.S. PATENT DOCUMENTS 5,583,432 A * 12/1996 Barnes .................. G01N 33/49
324/204

\* cited by examiner

*Primary Examiner* — George Manuel
(74) *Attorney, Agent, or Firm* — Marcus C. Dawes; Daniel L. Dawes

(57) ABSTRACT

A diffuse optical spectroscopic imaging (DOSI) apparatus for tissue spectroscopy measures absorption and scattering properties of tissue using multi-frequency frequency domain photon migration in a modular or networkable platform to provide full broadband information content. The apparatus includes: a broadband signal generator; a driver having an input coupled to the signal generator; a light source coupled to the driver, the light source for exposing the tissue to broadband modulated light at a plurality of wavelengths; an optical detector for receiving returned light from the tissue; an amplitude detection circuit communicated to the optical detector; a phase detection circuit communicated to the optical detector; and a plurality of filters and amplifiers, wherein the optical detector, amplitude detection circuit and phase detection circuit are interconnected with each other by corresponding ones of the plurality of filters and amplifiers to isolate signals and increase signal-to-noise ratio.

21 Claims, 10 Drawing Sheets

(51) Int. Cl.
*A61B 5/00* (2006.01)
*G01N 21/31* (2006.01)
*G01N 21/49* (2006.01)
*G01J 3/02* (2006.01)

(52) U.S. Cl.
CPC .......... *A61B 5/0091* (2013.01); *A61B 5/7225* (2013.01); *G01J 3/0264* (2013.01); *G01J 3/0272* (2013.01); *G01N 21/3103* (2013.01); *G01N 21/4795* (2013.01); *G01N 21/49* (2013.01); *G01N 2021/4735* (2013.01); *G01N 2021/4797* (2013.01)

(58) Field of Classification Search
CPC .......... G01J 3/0272; G01N 2021/4735; G01N 2021/4797; G01N 21/3103; G01N 21/47; G01N 21/4795; G01N 21/49
See application file for complete search history.

PORTABLE BROADBAND DIFFUSE OPTICAL SPECTROSCOPIC IMAGING (DOSI) DEVICE FOR NONINVASIVE TISSUE CHARACTERIZATION

RELATED APPLICATIONS

The present application is related to U.S. Provisional Patent Application, Ser. No. 61/752,702, filed on Jan. 15, 2013, which is incorporated herein by reference and to which priority is claimed pursuant to 35 USC 119.

GOVERNMENT RIGHTS

This invention was made with Government support under Grant Nos. CA105480 and RR001192, awarded by the National Institutes of Health. The Government has certain rights in this invention.

BACKGROUND

Field of the Technology

The disclosure relates to the field of portable broadband diffuse optical spectroscopic imaging device for noninvasive tissue characterization.

Description of the Prior Art

There are many prior art frequency-domain instruments that have been described in the literature (see Chance, B., Cope, M., Gratton, E., Ramanujam, N. & Tromberg, B. 1998 Phase measurement of light absorption and scatter in human tissue. *Review of Scientific Instruments* 69, 3457-81.) However, none of them use multi-frequency frequency-domain photon migration. None of them do this in a modular or networkable platform that allows for many smaller instruments to be linked together in lieu of a single larger instrument. None of them combine techniques to provide full broadband information content.

Frequency domain photon migration (FDPM) is an established technique for measuring tissue optical properties, i.e., absorption, $\mu_a$, and reduced scattering, $\mu_a'$. The FDPM technique uses light sources modulated at tens to hundreds of MHz to measure both the amplitude and the phase shift of multiply scattered light. Computational models are used to calculate absolute absorption and scattering tissue optical properties from these phase and amplitude measurements. Within the near-infrared infrared (NIR) spectral range (650 to 1000 nm) where FDPM is routinely employed, the tissue concentrations of oxygenated ($ctO_2Hb$) and deoxygenated hemoglobins (ctHHb), water ($ctH_2O$), bulk lipid, and other tissue constituents, both endogenous and exogenous, may be calculated from tissue absorption spectra. FDPM techniques can separate the effects of absorption from scattering using as little as a single spatial location, which is important because NIR light is strongly multiply scattered by tissues.

Technical challenges and practical limitations have prevented the widespread use of FDPM. In contrast to the complexity of FDPM, steady-state tissue spectroscopy methods are common because off-the-shelf systems are easily assembled from commercial vendors. Substantially fewer commercial FDPM devices are available, although at high cost. FDPM techniques are further complicated by introducing broadband FDPM methods, where the light sources are modulated over a range of frequencies. Increasing modulation bandwidth improves recovered optical property accuracy in both spectroscopy and imaging. A broadband FDPM instrument used in combination with a steady-state spectroscopy instrument to cover the entire MR spectral range has been involved in several pilot clinical studies. See for example, Quantitative Broadband Absorption and Scattering Spectroscopy in Turbid Media by Combined Frequency-Domain and Steady State Methodologies, U.S. Pat. No. 7,428,434, incorporated herein by reference. One embodiment of this instrument is the laser breast scanner (LBS) which represents a fairly standardized instrument platform. The core of the FDPM component of this instrument consists of a conventional network analyzer to generate and detect modulated radio frequency (RF) currents. For each laser diode (currently six), the network analyzer generates RF frequencies in series from 50 MHz to 1 GHz at 15-dBm electrical power. Laser diodes are DC-biased using a separate current source. An avalanche photo diode (APD) detects the diffuse reflectance from the tissue, sends the RF electronic signal back to the network analyzer, and compares this signal to a reference. The network analyzer measures the reflectance attenuation and phase shift between transmitter and receiver as functions of modulation frequency.

However, this network-analyzer-based FDPM instrument suffers from a number of technical limitations. First, the instrument is constructed using general-purpose commercial electronics and is therefore both expensive ($60 k total) and large in size. Second, the current FDPM instrument has run up against temporal performance limits. Sweeping 401 modulation frequencies takes approximately 1 s, but most of this time is wasted due to communication delays. Third, the high cost and large size of the instrument impedes expansion into multichannel imaging devices and increases barriers to access.

BRIEF SUMMARY

The diffuse optical spectroscopic imaging (DOSI) device of the illustrated embodiments of the invention is a quantitative spectroscopy instrument which measures the absorption and scattering properties of tissues and/or turbid media. These absorption and scattering properties are dependent upon the functional and structural composition of the sample. The use of non-ionizing radiation probes the below the surface of the sample noninvasively. While the idea of optical spectroscopy in tissues and turbid media is not unique, we present a unique compact device platform that can be readily commercially replicated for widespread clinical use, as opposed to "perennial prototype" or custom systems used in large research centers, hospitals, and/or analytical labs.

The device is a broadband quantitative spectrometer that works under the principles of diffuse optical spectroscopic imaging (DOSI). The principles of DOSI involve frequency-domain and, steady-state spectroscopy. Spectroscopic analysis methods are employed to convert the measured optical signals into absorption and scattering spectra and chemical composition, including the concentrations of endogenous and/or exogenous constituents of the sample.

What is disclosed is a compact modular platform which has been developed to lower technical and economic barriers to access for this technology. We have published extensively on the DOSI platform using a network-analyzer based instrument. The advantage here is that the off-the-shelf RF electronics used in the network analyzer were condensed into a circuit board-level instrument. This is the only networkable, scalable compact, miniature multi-frequency and spectral broadband spectrometer currently designed. The device provides very high portability yet retains the ability to give high information content.

A board-level broadband frequency domain photon migration (FDPM), mini-FDPM, instrument has been constructed to replace a conventional network analyzer based FPM instrument. The mini-FDPM instrument with four wavelengths: 681, 783, 823, and 850 nm, matches or exceeds conventional FDPM instruments in performance, namely −120 dBm noise level, 100 dB dynamic range and bandwidth of 1 GHz, and recovers the same optical properties within about 6% in absorption and 4% in reduced scattering for liquid phantoms covering a wide range of relevant optical properties. Compared to the conventional FDPM instrument, the mini-FDPM instrument is more than 5 times faster (about 200 ms per 401 modulation frequencies) and several orders of magnitude less in size and cost.

Standard fiberoptic-based probes can be used with the mini-FDPM instrument, which increases applications in a number of clinically relevant measurement scenarios. By drastically reducing size and cost, FDPM miniaturization lowers barriers to access and helps to promote the use of FDPM in clinical research problems. The mini-FDPM instrument forms the core of a modular broadband diffuse optical spectroscopy instrument that can be used for a variety of problems in imaging and quantitative analysis. Its uses include, but are not limited to, breast cancer detection, therapeutic monitoring, critical care medicine, exercise physiology, functional brain monitoring, and vascular reactivity assessment. The mini-FDPM instrument can also be used in conjunction with endoscopic probes for internal organ measurements, and in any turbid in vitro system where quantitative analysis of absorption, scattering, and/or fluorescence is required.

In summary, the illustrated embodiments of the invention include a diffuse optical spectroscopic imaging (DOSI) apparatus for quantitative spectroscopy to measure absorption and scattering properties of turbid samples using multi-frequency frequency domain photon migration in a modular or networkable platform to provide full broadband information content. The apparatus includes; a broadband signal generator; a driver having an input coupled to the signal generator; a light source coupled to the driver, the light source for exposing the tissue to broadband modulated light at a plurality of wavelengths; an optical detector for receiving returned light from the tissue; an amplitude and/or phase detection circuit communicated to the optical detector; and a plurality of filters and amplifiers, wherein the optical detector and amplitude and/or phase detection circuit are interconnected with each other with a corresponding plurality of filters and amplifiers to isolate signals and increase signal-to-noise ratio. The local signal generator generates a fixed high frequency signal (e.g. 3-GHz signal) and a swept broadband signal in a lower frequency band (e.g. 2.00 to 2.99 GHz), and mixes the fixed high frequency signal with the swept broadband signal to modulate the light source, which has a modulated optical output in a swept modulated frequency band that corresponds to the high-low difference frequency. For example, in the case of a fixed 3 GHz signal and a swept 2.00 to 2.99 GHz broadband signal, this would result in a 10 MHz to 1 GHz system for light modulation. The actual broadband oscillator frequencies and high frequency local oscillator frequency can vary depending on the instrument demands and specific components. The frequencies of the fixed signal and a swept signal of the broadband signal generator are user selectable.

The signal generator includes a temperature-compensated crystal (TCXO), voltage-controlled (VCO), phase-locked loop (PLL) oscillator generating a precise and stable frequency.

In one embodiment the light source includes four lasers with wavelengths 681, 783, 823, and 850 nM, in general, the light source includes a plurality of lasers or modulated light sources, each with different or identical wavelengths.

The light source further includes a feedback photodiode optically coupled to the light source; and an automatic power control (APC) circuit having a digital potentiometer coupled to the feedback photodiode to compare a monitored current in the light source with a voltage derived from the digital potentiometer to control laser optical power, so that the light source can emit a precise power level without fluctuation.

The apparatus further includes an automatic current control (ACC) circuit using precise current monitoring feedback from the driving current.

The optical detector includes a heterodyne circuit and where the optical detector generates RF photocurrents from the light detector which are detected using the heterodyne circuit to demodulate the RF photocurrents by mixing the RF photocurrents with a broadband oscillating signal (e.g., but not limited to, 1.955-GHz to 2.945-GHz) to generate an intermediate frequency IF (e.g. 2.955 GHz), which is filtered with a high Q dielectric resonator filter and down converted to a low frequency signal (e.g. 45 MHz) to eliminate cross-talk with a source band signal modulating the light source. The actual broadband oscillating signal, IF signal, and down conversion frequency can vary depending on the instrument demands and specific components.

The amplitude and/or phase detection circuit comprises a detector to measure the power and phase shift and/or the real and imaginary components of the down converted signal (e.g., 45-MHz) respectively.

The apparatus further includes a multipart A/D control unit with an integrated fast Ethernet, USB, digital, and/or wireless interface to control the signal generator, driver, light source, optical detector, amplitude and/or phase detection circuit and the plurality of filters and amplifiers necessary to gather data.

The illustrated embodiments of the invention further includes a plurality of FDPM and/or diffuse optical spectroscopic imaging (DOSI) apparatus so that a plurality of FDPM and/or diffuse optical spectroscopic imaging (DOSI) systems can be networked together to operate as one larger, integrated instrument.

The illustrated embodiments of the invention further includes one or more light sources at a plurality of optical wavelengths that are time-independent and/or modulated at frequencies that are lower than the high frequency band used for light modulation of the FDPM system. Wavelength selection of these light sources can be accomplished using a spectrometer system and/or a combination of conventional switching, dispersion, or temporal/spatial encoding strategies to enhance overall spectral bandwidth and/or spectral information content response at a plurality of optical wavelengths.

The signal generator modulates the light source at a fixed frequency and/or over a selectable and controllable set of and/or range of frequencies, where the signal generator comprises a fixed frequency oscillator, a variable frequency oscillator and a mixer, wherein an output of the fixed frequency oscillator is mixed with an output of the variable frequency oscillator, the difference between the outputs varying over a broad range of frequencies and being provided as an output of the mixer to modulate the light source.

The signal generator, driver, light source, optical detector, amplitude and/or phase detection circuit are implemented in modular interconnected boards.

The optical detector can be adapted for use in measurement of any one of a plurality of tissue types or environments, including, but not limited to breast, brain, bone, joints, muscle, and skin tissues, endoscopic measurements, splanchnic tissues, and/or measurements conducted on any type of optically turbid specimen in any environment. The optical detector can be placed in contact/proximity with the measured specimen and/or be used in conjunction with a light guide (e.g. fiber optic) and/or lens system to transmit the optical signals to the optical detector.

The optical detector includes an up-conversion circuit to increase modulation frequencies to center on the up converted frequency (e.g. 2.955 GHz), a dielectric filter coupled to the up-conversion circuit (e.g. 2.955 GHz), and a down-conversion circuit using a high frequency local VCO (e.g. 3 GHz) coupled to the dielectric filter to return to the down converted IF modulation frequencies (e.g. 45 MHz). The actual broadband oscillating signal, IF signal, and down conversion frequency can vary depending on the instrument demands and specific components. The up-conversion heterodyne circuit employs a broadband oscillating signal, where the intermediate RF signal, and down conversion frequency of the oscillating signal from the oscillator are user selectable.

The illustrated embodiments of the invention also extend to a method including the steps of: generating diffuse optical spectroscopic spectra and/or images using a diffuse optical spectroscopic imaging (DOSI) apparatus for quantitative spectroscopy to measure absorption and scattering properties of tissue and/or turbid media using multi-frequency frequency domain photon migration either alone or in combination with time-independent steady state spectroscopy in a modular and/or networkable platform to provide quantitative spectral information content from one or more locations in the measured sample; and combining the diffuse optical spectroscopic image (DOSI) with a structural and/or functional image to assign and/or co-register DOSI-derived information content to a selected portion of interest in the complementary imaging modality.

While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112. The disclosure can be better visualized by turning now to the following drawings wherein like elements are referenced by like numerals.

The disclosure and its various embodiments can now be better understood by turning to the following detailed description of the preferred embodiments which are presented as illustrated examples of the embodiments defined in the claims. It is expressly understood that the embodiments as defined by the claims may be broader than the illustrated embodiments described below.

DETAILED DESCRIPTION OF THE PREFERRED EMBODIMENTS

Figure 1:
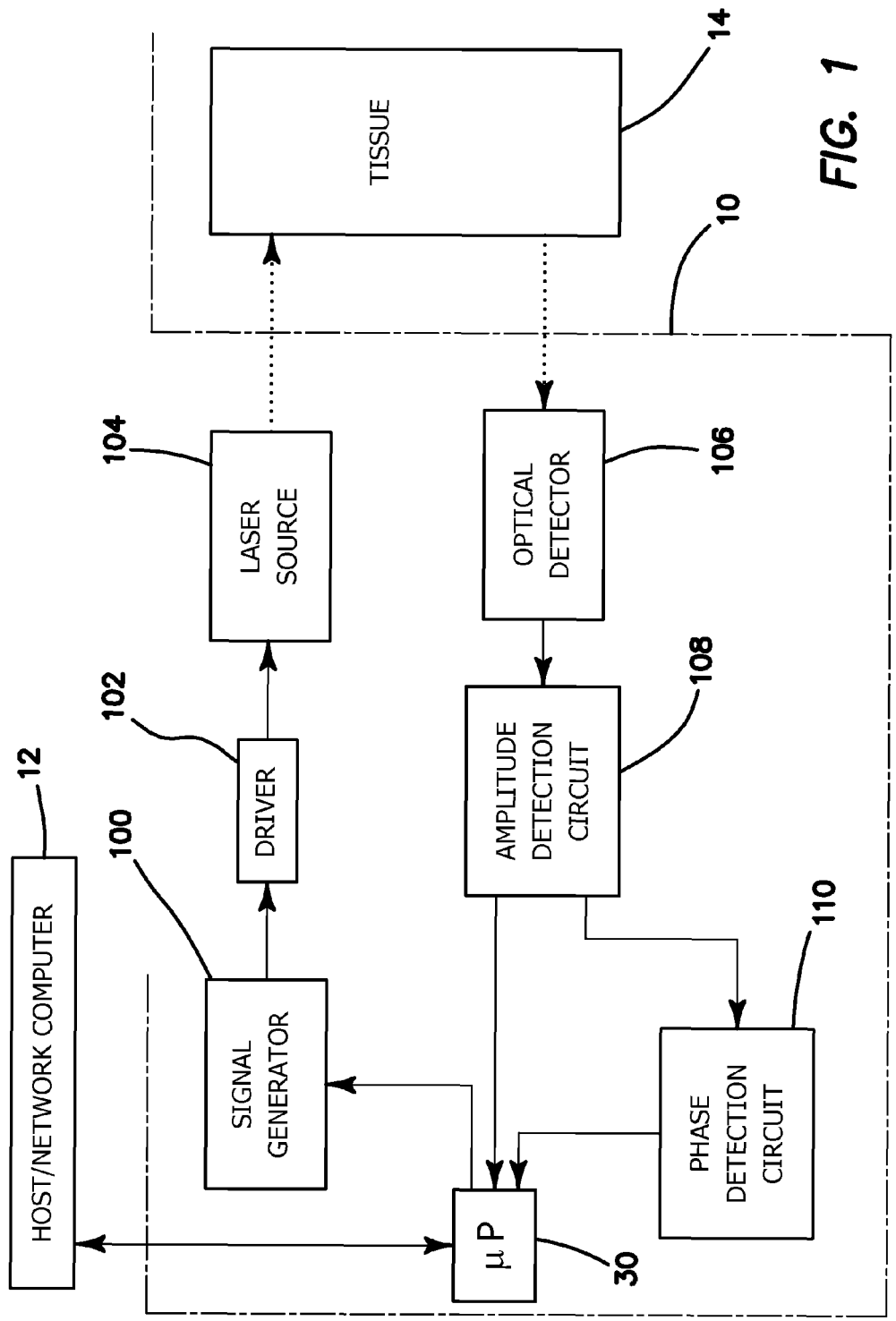
FIG. 1 is a high level block diagram of the major circuit elements of the illustrated embodiment of the invention.
Figure 2:
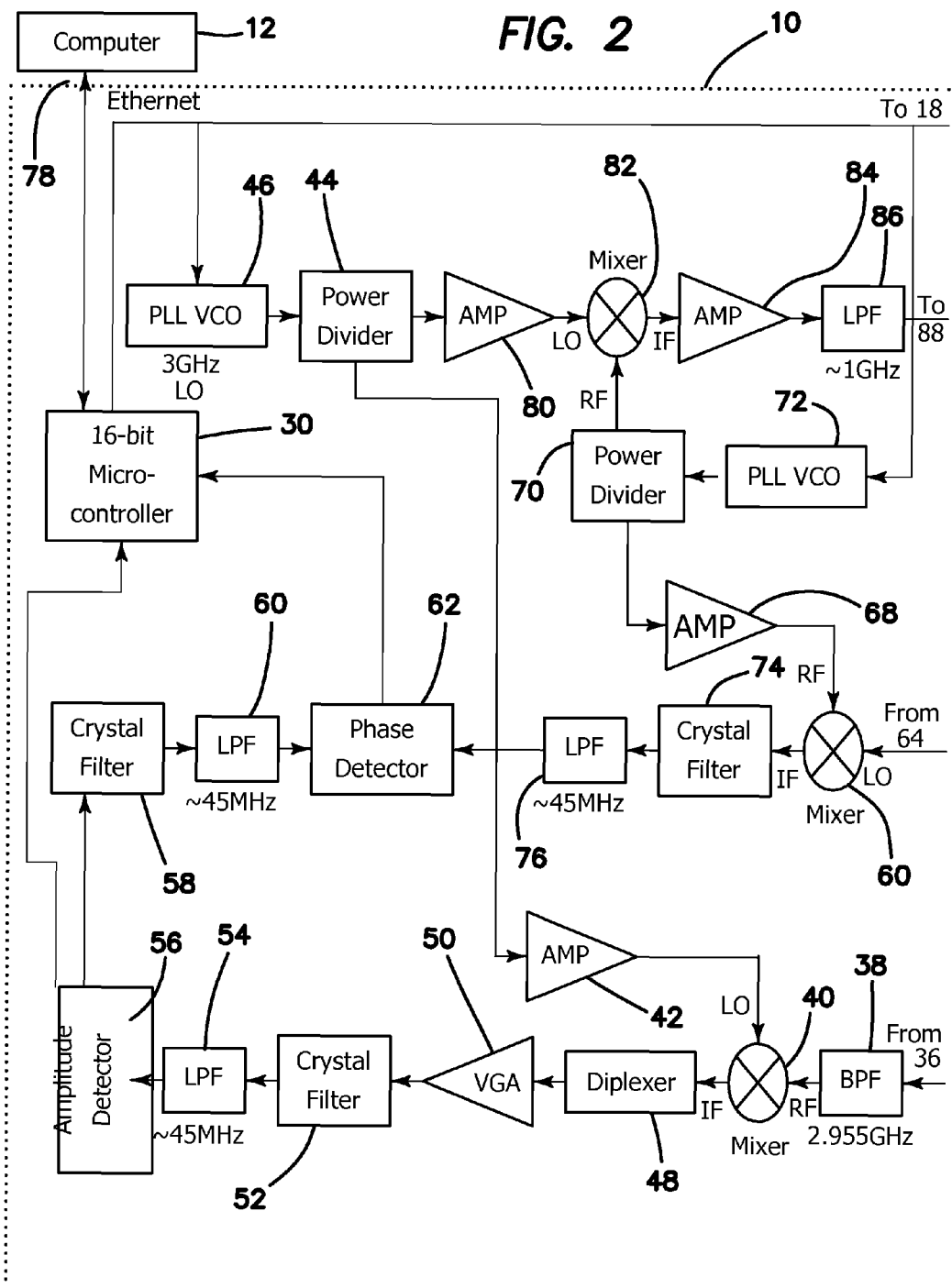
FIG. 2 is a detailed block diagram of the circuit blocks of the illustrated invention.
Figure 2:
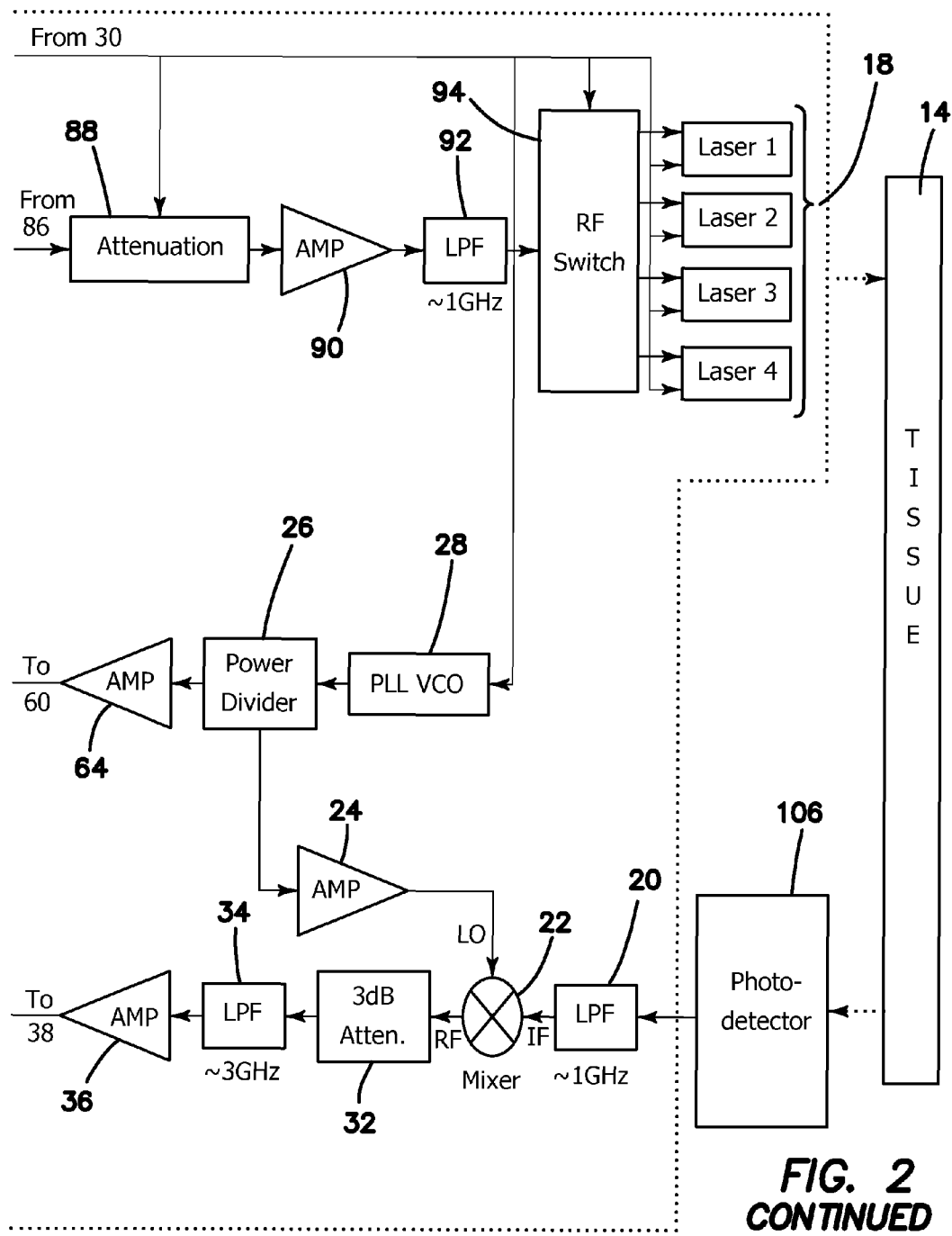

One goal of the illustrated embodiments is to construct a miniature version of this LBS instrument without sacrificing any broadband information content, either spectral or temporal. The core element enabling realization of this goal is a board-level FDPM instrument, mini-FDPM, as shown in FIGS. 1 and 2. To reduce cost and size, we replaced the expensive, bulky network analyzer with a compact, custom designed frequency-sweeping circuit. By replacing commercial off-the-shelf technologies, i.e., current sources, RF switches, and other circuit components with chip-based broadband communication electronics and processors, we miniaturized the FDPM instrument from a cart-based rack costing five digits down to a portable unit that costs about $500 in parts in 2013 prices.

Our broadband circuit 10 modulates the optical signals from 10 MHz to 1 GHz. A built-in 100 base/T Ethernet interface 78 supports fast data transfer rates and connection with an external host computer or other mini-FDPM instruments to form a network of such instruments. The measurement of 401 modulation frequencies was reduced from 1 s/wavelength down to 0.2 s/wavelength. The reduction in the number of frequencies results in a linear decrease in measurement time.

As depicted in the high level block diagram of FIG. 1 the mini-FDPM instrument is comprised of a signal generator 100 connected to a driver 102 which drives a laser light source 104 for exposing tissue 14. An optical detector 106 optically detects a returned optical signal from tissue 14, which is then measured in an amplitude detection circuit 108, and a phase detection circuit 110. Each component is connected with each other by electronic filters and amplifiers (not shown in FIG. 1, but described in greater detail below in relation to FIG. 2) to isolate signals and increase the signal-to-noise ratio. Amplitude detection circuit 108, phase detection circuit 110 and signal generator 100 are communicated with microprocessor 30 which provides overall circuit control, synchronization, parameter settings and bidirectional communication with an external host or network computer 12.

Figure 3:
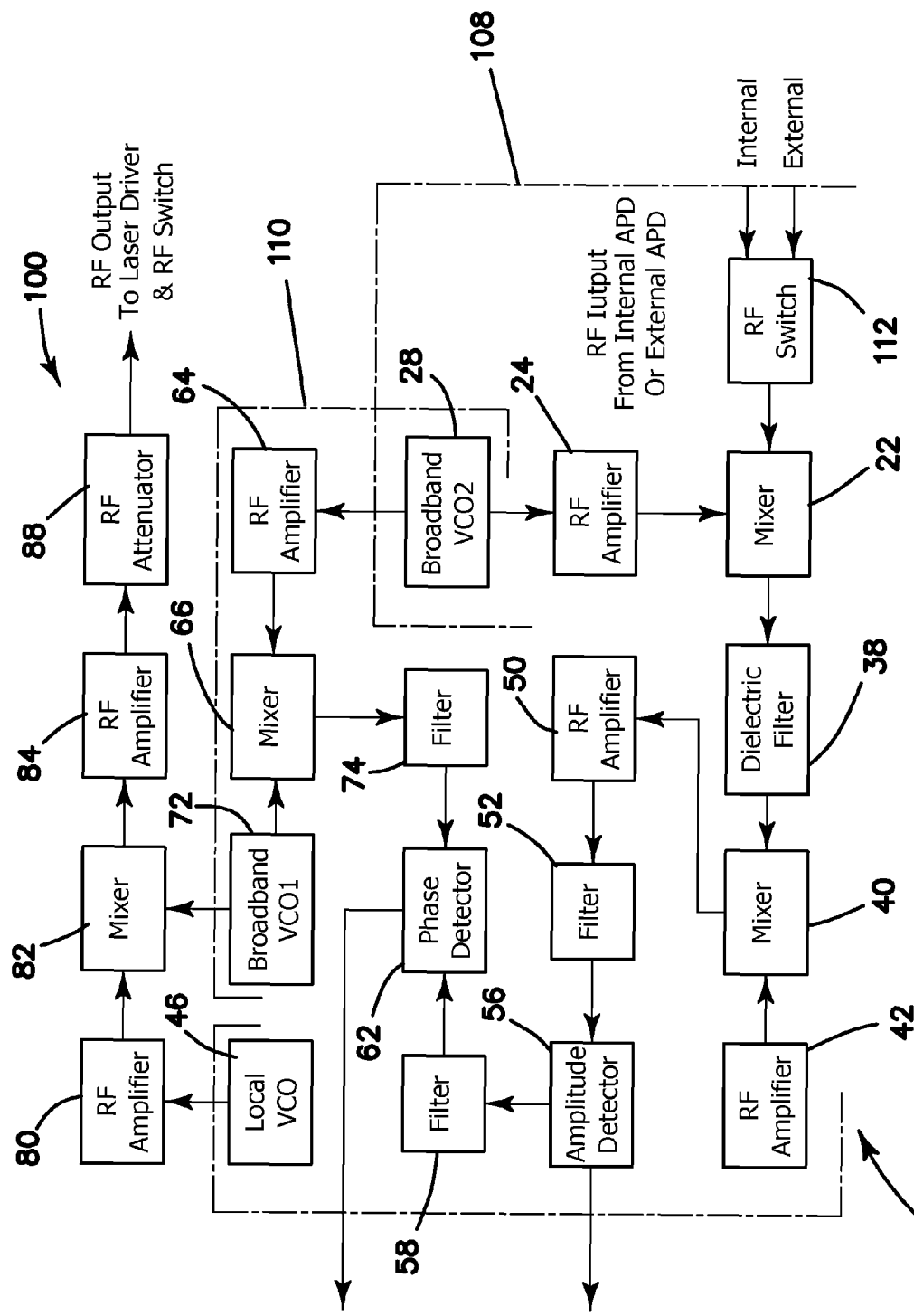
FIG. 3 is a block diagram of the principal components of the signal generator, amplitude detector and phase detector portions of the illustrated invention.

The overall organization of circuit 10 is shown in greater detail in the embodiment of FIG. 3. In this embodiment an RF switch 112 is provided for selectively switching between the RF signal from either an internal or external the APD or photodetector circuit 16 or APD. The reference numerals of the corresponding primary circuit components in FIG. 2 have been utilized in FIG. 3 to make a comparison of the diagrams clearer. A number of secondary circuit elements have not been shown in FIG. 3 and will be discussed in greater detail in FIG. 2 below.

The source frequency band (10 MHz to 1 GHz) is too broad to be generated directly from oscillators in a cost effective manner, so instead, a fixed 3-GHz frequency generated by local VCO 46 is mixed with a variable frequency in the 2 to 2.99 GHz and 1.955 to 2.945 GHz bandwidth from broadband oscillators 72 and 28 respectively. Synchronized phase-locked bop (PLL) oscillators 28, 46, 72 shown in FIGS. 2 and 3 in signal generator 100 and optical detector 106 in FIG. 1 each generate precise and stable frequencies by combining the flexibility of a voltage-controlled oscillator (VCO) with the stability of a 10-MHz temperature-compensated crystal oscillator (TCXO) (not shown) which is coupled to each of the phase locked loop oscillator 28, 46, 72 for use as a stable synchronizing reference signal. The wavelengths of the four lasers 18 included in laser source 104 are 681, 783, 823, and 850 nm, which matches the laser diodes in the comparable network analyzer-based FDPM instrument.

Figure 10:
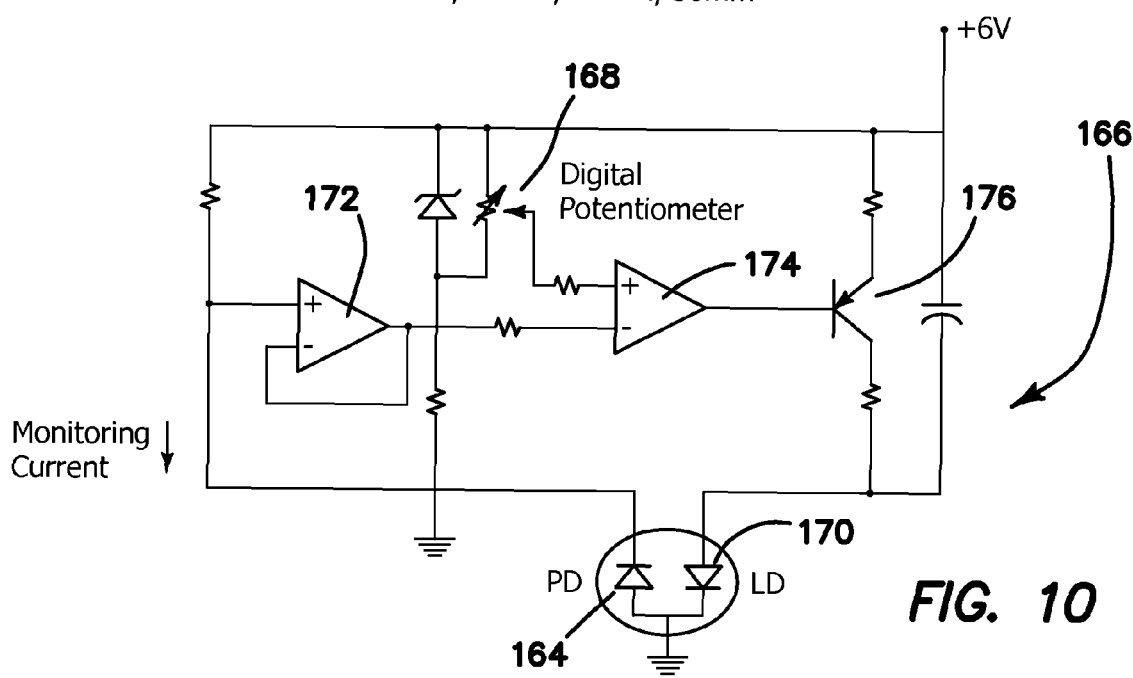
FIG. 10 is a schematic diagram of one embodiment of the APC utilized in the illustrated embodiment to provide precise maintenance of the power level of the laser diodes.

We implemented two different types of automatic power control (APC) circuits (not shown) in laser source 104, one for the common laser diode cathode and photodiode anode-on-case (CCA) type laser, and the other for the common laser diode anode and photodiode cathode-on-case (CAC) type laser. The APC circuit 166 in FIG. 10 uses precise power monitoring feedback from a photodiode 164 within the laser diode package 104. The APC 166 compares the voltage induced by the monitoring current from the photodiode 164 with the voltage induced by a digital potentiometer 168 in the APC 166. Photodiode 164 receives an optical feedback from laser diode 170. The feedback from photodiode 164 is coupled to signal conditioning amplifier 172. By controlling the digital potentiometer value with a microprocessor 30 in FIG. 2, we can carefully control laser optical power. The set value in digital potentiometer 168 is compared against the monitored current fedback from photodiode 164 in differential amplifier 174, whose output is provided to the base of transistor driver 176 through which laser diode 170 is powered. With the APC 166, we can maintain a precise emitting optical power level.

In signal generator 100 the 3 GHz fixed frequency signal is generated by oscillator 46 in FIG. 3, amplified by RF amplifier 80 and combined in mixer 82 with the output of 2 to 2.99 GHz broadband oscillator 72 to provide the 10 MHz to 1 GHz as an intermediate frequency (IF) signal to RF amplifier 84. The amplified IF signal (RF output signal) is then attenuated by attenuator 88 and provided to driver 102 and then to laser source 104. The outputs of the lasers are thus modulated at the IF (RF output) frequencies according to the control of broadband oscillator 72 by microprocessor 30 which is coupled thereto.

The average laser power was 20 mW. RF photocurrents from the avalanche photodiodes (APD) are detected in the circuitry in photodetector 16 using a custom heterodyne circuit shown in FIGS. 2 and 3. The demodulated RF signal from photodetector 106 or 45 MHz IF modulated output from the APD 16 mixes in mixer 22 with the amplified output of a 1.955-GHz to 2.945-GHz oscillator 28 coupled through RF amplifier 24 and is up-converted to the RF frequency (RF). The RF signal is then filtered by high Q dielectric resonator filter 38 and down converted to 45 MHz IF in mixer 40 coupled to 3 GHz local oscillator 46 through RF amplifier 42 to eliminate cross-talk with the source band signal, which is modulating the lasers in circuit 10. This heterodyne structure reduces spurious signals with a single filter 38 despite the broad frequency range of the photocurrents. A logarithmic amplifier or amplitude detector 56 and phase detector 62 then measures the power or amplitude and the phase shift of the 45-MHz signal respectively. The amplitude is picked off the logarithmically amplified signal with an envelope detector and the phase shift is measured by comparison to the synchronized 3 GHz fixed frequency utilized in circuit 10. The output of mixer 40 is amplified by RF amplifier 50, filtered by filter 52 and input into amplitude detector 56, whose output is provided to microprocessor 30. The output of amplitude detector 56 is also provided through filter 58 to phase detector 62, whose output in turn is also provided to microprocessor 30. Phase detector 62 takes its measuring phase marker from the filtered output of mixer 66 through filter 74, which mixer 66 takes its inputs in turn from broadband oscillator 72 and broadband oscillator 28 through RF amplifier 64. A 16-bit multipart control unit or microprocessor 30 with an integrated fast Ethernet (10/100 base/T) interface controls the system hardware and gathers the data from the amplitude and phase detector circuits 56 and 62 respectively with a built-in analog-to-digital converter (ADC).

Figure 4:
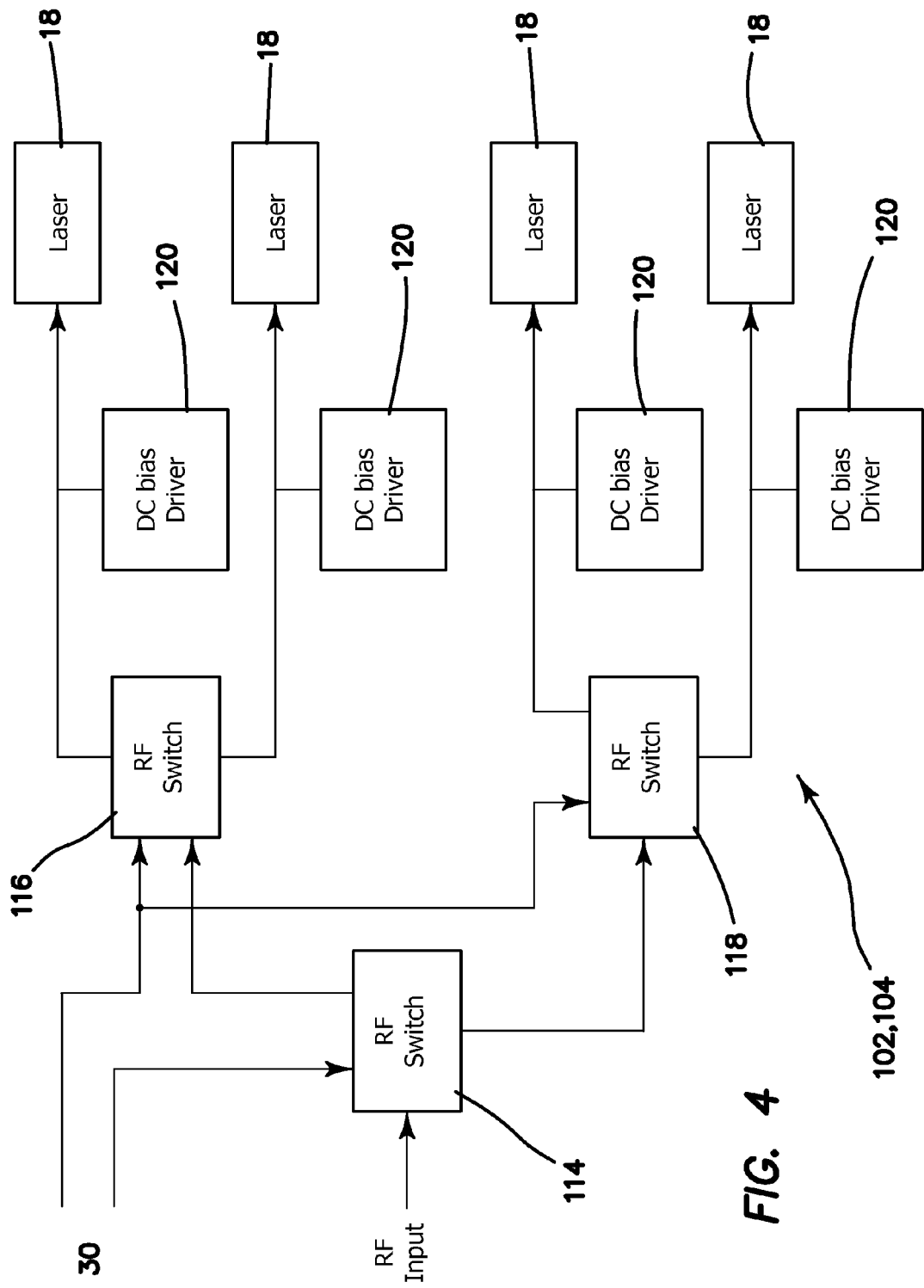
FIG. 4 is a block diagram showing the organization of one embodiment of the laser driver and laser bank.

Driver 102 and laser source 104 is shown in more detail in the block diagram of FIG. 4. The RF modulating signal from signal generator 100 is coupled to a bistate RF switch 114, whose outputs in turn are coupled each to bistate RF switches 116 and 118. The two outputs of RF switches 116, 118 are coupled to corresponding ones of lasers 18, which are each provided with a corresponding DC bias driver 120. RF switches 114, 116, 118 form a switching tree controlled by processor 30 to selectively activate one of lasers 18, which in the illustrated embodiment each operate at different wavelengths.

Figure 6:
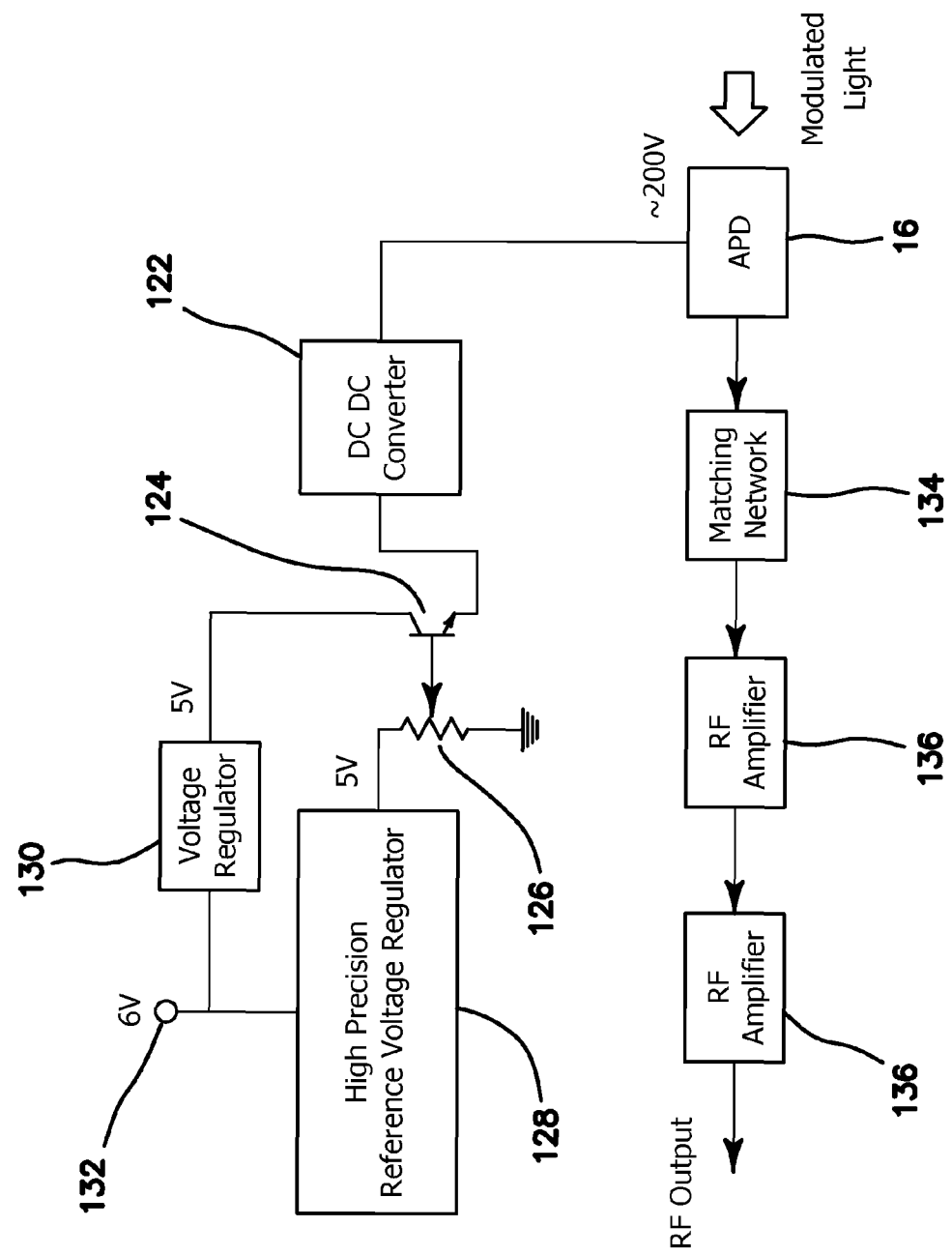
FIG. 6 is a block diagram of the components of one embodiment of the optical detector employed in the illustrated invention.

Optical detector 106 is illustrated in more detail in the block diagram of FIG. 6. APD 6 is powered by a DC/DC converter 122 whose input is the emitter of transistor 124. The collector of transistor 124 is coupled to a 5 volt voltage regulator 130 supplied by the 6 volt power bus 132 of circuit 10, connected to a battery or other power source. The base of transistor 124 is coupled to potentiometer 126 coupled in turn to a high precision 5 v 1 voltage regulator reference connected to power bus 132. Potentiometer 126 is either manually set or is digitally controlled by microprocessor 30. As a result 200 v DC is supplied as a precisely stabilized and calibrated voltage source to APD 16 to maintain the calibration of the photodetectors. The output of APD 16 is coupled through a matching network 134 to RF amplifiers 136 for input to amplitude detection circuit 108.

Given the general description of the organization of system 10 and its performance above, return now to FIG. 2 for a more detailed consideration of system 10. System 10 is digitally coupled to a computer 12 and optically coupled to the target tissue 14. Returned modulated light from tissue 14 is received by photodetector 16, which in turn is coupled by an analog line to system 10. Light is incident on tissue 14 from lasers 18, in FIG. 2, laser bank or source 18 is illustratively shown as including four lasers, but the number is arbitrary and may be less than or more than four. The 3 GHz signal from phase locked loop variable oscillator 46, controlled by microcontroller 30, is coupled through power divider 44 to 17 db gain amplifier 80. The output of amplifier 80 is mixed in mixer 82 with an RF signal from power divider 70 taking its signal from 2 GHz-2.99 GHz broadband phase locked loop variable oscillator 72, controlled by microcontroller 30. The output of mixer 82 is an IF signal provided to 20 dB gain amplifier 84, whose output is coupled to 1 GHz low pass filter 86. The output of filter 86 is fed to 31.5 dB variable attenuator 88 with 0.5 dB steps controlled by microcontroller 30. With this attenuator, we can modulate the lasers without saturation, i.e., without clipping the laser output. The output of attenuator 88 is input to 18 dB gain amplifier 90 and thence to 1 GHz low pass filter 92. The output of filter 92 is then provided to RF switch 94, controlled by microcontroller 30, to selectively drive laser source 18.

The modulated output signal from photodetector 16 is coupled to a low pass filter 20 having a 1 GHz band pass. The output of filter 20 is at an intermediate frequency, IF, of 45 MHz and is provided to mixer 20, whose other input is the output of 17 dB gain amplifier 24. Amplifier 24 takes its input from power divider 26, which is driver by synchronized phase locked loop variable control oscillator 28, which is a broadband oscillator generating outputs between 1.955 GHz and 2.945 GHz, controlled by microcontroller 30.

The up-converted RF output of mixer 22 is coupled to 3 dB attenuator 32 and then to low pass filter 34 having a 3 GHz band pass. The output of filter 34 is coupled to 20 db gain amplifier 36 whose output is coupled to band pass filter 38 centered on 2.955 GHz. The RF output of filter 38 is then coupled to mixer 40, whose other input is coupled to 17 dB amplifier 42. The input of amplifier 42 is coupled to power divider 44 and thence to the output of synchronized phase locked loop variable control oscillator 46, generating an output centered around 3 GHz, which in turn is controlled by 16 bit microcontroller 30.

The output of mixer 40 is an IF signal provided to diplexer 48 and thence to variable gain amplifier 50 operating between −10 to 40 dB gain depending on the power level of IF signal. The other input to diplexer 48 is terminated to 50 ohm providing matching impedance for broad bandwidth. The output of amplifier 50 is coupled to crystal controlled filter 52 centered on 45 MHz with a 30 kHz bandpass. The output of filter 52 is coupled to low pass filter 54, which is centered on 45 MHz. The output of filter 54 is then coupled to envelope detector 56 whose output is coupled to microprocessor 30 and is also supplied to crystal filter 58 centered on 45 MHz with a 30 kHz bandpass. The output of filter 58 is filtered again by low pass filter 60 centered on 45 MHz, whose output is coupled to phase detector 62, which is also controlled by 16 bit microcontroller 30.

A portion of the output of oscillator 28 is coupled through power divider 26 to 17 dB amplifier 64 to mixer 66, whose other input is coupled to the RF signal from 17 dB amplifier 68. Amplifier 68 takes its signal from power divider 70 and synchronized RF broadband phase locked loop variable controlled oscillator 72 operating between 2 GHz and 2.99 GHz. Oscillator 72 is controlled by 16 bit microcontroller 30. The IF output of mixer 66 is coupled to crystal filter 74 centered on 45 MHz with a passband of 30 kHz, whose output in turn is coupled through low pass filter 76 centered on 45 MHz to phase detector 62 to provide the reference phase signal so that phase shifts can be measured.

The output of phase detector 62 is supplied to microprocessor along with the output of the amplitude detector 56; these outputs being the data points, which are then supplied to host computer 12 for further data reduction to calculate the optical absorption and scattering coefficient values. These data points along with data returned from a conventional broadband continuous wave spectrum analyzer coupled to host computer 12 operating in parallel with circuit 10 allows the optical spectra to be generated in host computer 12 and from that chromophore identification and quantification in tissue 14. From such data tomographic images can also be generated from tissue 14.

It is to be noted that the various components of circuit 10 are, provided on modular boards so that portions of the circuit 10 can be changed out for either redesign or maintenance purposes by simply replacing the entire modular board as is the conventional practice with personal computers. For example, the laser driver 102 and laser source 104 are provided on a separate board, so that different wavelength laser banks can be changed out simply by removing the existing board and plugging in a replacement board without any circuit redesign or construction required. Similarly, optical detector 106 is provided on a separate plug-in board for ease of change-out between different detector subsystems as may be advantageous. Further, although the illustrated embodiment has been shown in FIG. 2 as organized in separate circuit blocks, it is within the contemplation of the invention that the concept of the illustrated invention can be implemented in custom-designed integrated circuit chips for even further space and cost savings.

It can now be appreciated that by using two VCOs (local VCO 46 and broadband VCO 28, 72) we are able to easily generate a very broad low frequency band (10 MHz to 1 GHz) for modulation. Using PLL VCOs with TCXO reference generates precise frequencies. We can achieve fast lock times in the PLLs due to 2-3 GHz high frequency VCOs. We have employed a unique detection circuit schematic to filter input frequencies, namely to up-convert to 2.955 GHz and down convert with 3 GHz local VCO which allows us to use a 2.955 GHz dielectric filter. By using a 45 MHz intermediate frequency we are also allowed to use conventionally available crystal filters. The filter design reduces harmonic frequencies. Power adjustment in the amplitude detector 56 allows us to realize a 100 dB dynamic range in amplitude. The use of an RF switch 112 at the front end of the optical detector circuitry allows dual RF inputs from internal or external photo-optical subsystems.

The performance levels of the mini- and network-analyzer FDPM instruments are similar. The noise levels of network analyzer FDPM and mini-FDPM instruments are −95 dBm and −88 dBm, respectively. However, the overall system noise level is currently detector limited by the APD to −78 dBm. The dynamic range of the instruments are 120 dB (network analyzer) and 100 dB (mini-FDPM). Similarly, the dynamic range is again detector limited (85 dB). Both designs use the same handheld probe; this handheld probe included source optical fibers for the lasers and an APO. The stability of both instruments was measured using the same APD by fixing the handheld probe onto a standard tissue phantom and measuring continuously for 1 h. The phase drift was 0.02 deg and 0.13 deg for the standard and mini-FDPM instruments, respectively. The mini-FDPM phase drift compares favorably with the first-generation FDPM phase drift (0.3 deg over 30 min). The amplitude drift was 2% and 6% for the standard and mini-FDPM instruments, respectively. This is to be compared with a 3% drift aver 30 min for the first-generation FDPM instrument. The drift errors translated into optical properties of 1.3% and 3% for the standard and mini-FDPM instruments, respectively.

The lower drift of the standard instrument is likely due to the individual temperature control circuits for each laser diode. Implementing a similar strategy for the mini-FDPM instrument should significantly reduce the drift.

We designed phantom experiments to characterize the performance in the recovery of optical properties of the mini-FDPM instrument of the illustrated embodiments relative to the standard FDPM instrument. We fabricated 10 homogeneous liquid phantoms. Liquid phantoms (1000 mL volume each) were made with varying concentrations of Lyposin (Abbott Laboratories, Chicago, Ill.) as the scattering agent and a water-soluble dye, Nigrosin (Sigma, St. Louis, Mo.), as the absorbing agent. The phantoms were designed to emulate the optical properties of tissues typically encountered by the LBS: normal breast (50 ml Lyposin, 3 ml Nigrosin), normal brain (60 ml Lyposin, 12 ml Nigrosin), muscle and breast tumors (30 ml Lyposin, 14 ml Nigrosin), and bone (70 ml Lyposin, 4 ml Nigrosin).

Figure 5A:
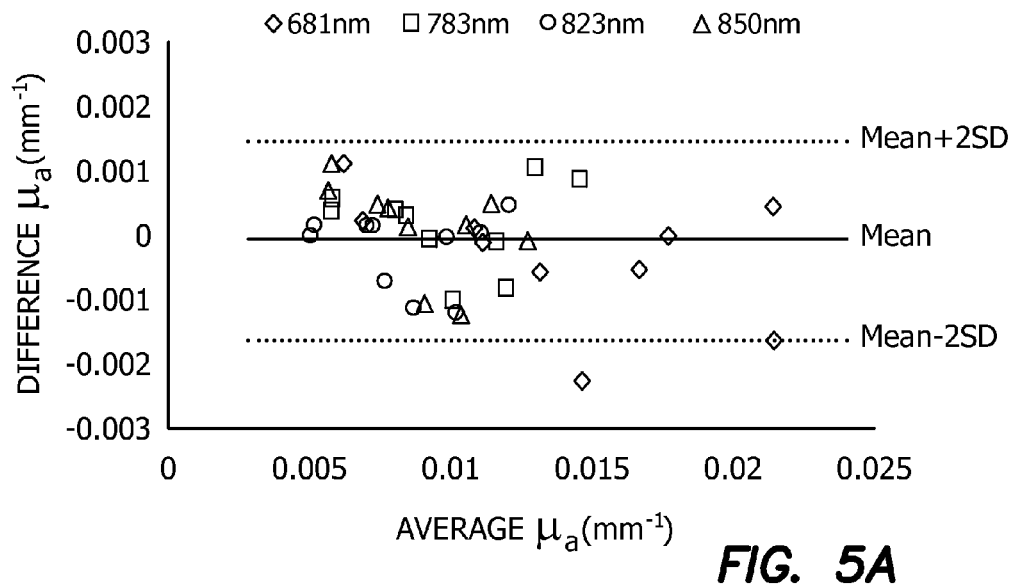
FIGS. 5a and 5b are graphs of the recovered optical properties of 10 liquid phantoms using both standard and mini-FDPM instruments. The comparisons are plotted using Bland and Altman plots for the recovered $\mu_a$ in FIG. 5a and $\mu_s'$ in FIG. 5b. In general, the mini-FDPM instrument reliably recovered the same $\mu_a$ and $\mu_s'$ values as the standard FDPM instrument over a wide range of physiologically relevant optical properties.
Figure 5B:
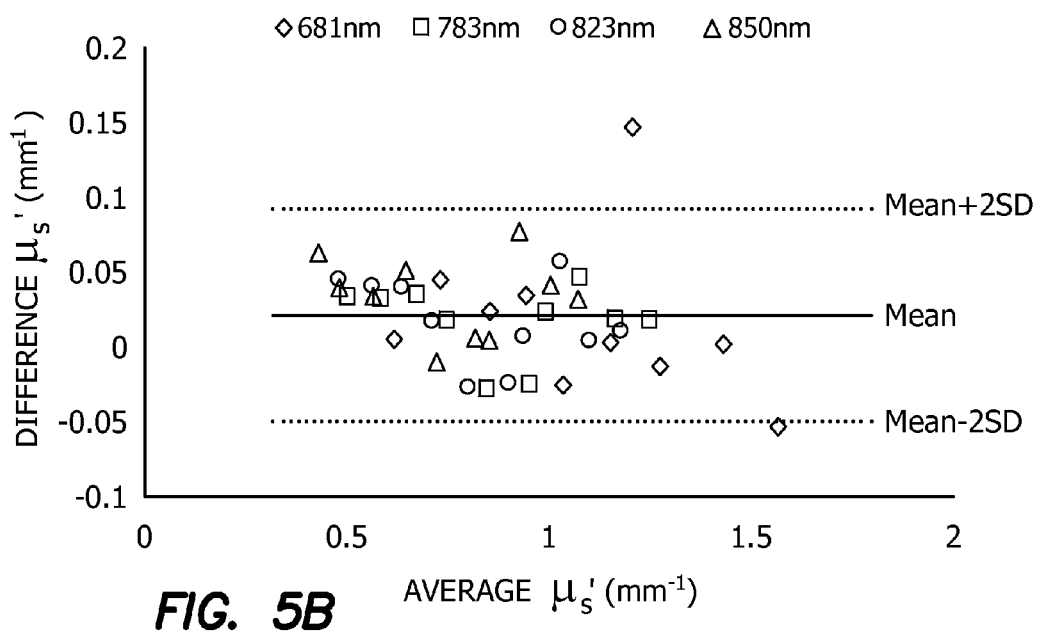

We used the same handheld optical probe, for both systems. In this way, the performance of the FDPM hardware could be evaluated independently of the choice of detectors, source fibers, and probe coupling. All FDPM measurements were taken with a single source-detector distance in a reflectance semi-infinite geometry. The optical fibers were positioned on the liquid phantom surface. Instrumental phase and amplitude artifacts were calibrated using a separate liquid phantom, which was also constructed from Intralipid and Nigrosin, with known optical properties. FIG. 5 shows the recovered $\mu_a$ and $\mu_s'$ values for both FDPM instruments. We used a Bland and Altman plot to compare the phantom optical properties measured by both instruments. The Bland and Altman plot compares the mean of the two measurements versus the difference of the two measurements and is generally preferred to correlation plots. The results revealed that the mini-FDPM instrument is a good substitute for the standard FDPM instrument. For all wavelengths, the average deviation between $\mu_a$ values was 0.0006 mm$^{-1}$, and 0.03 mm$^{-1}$ for $\mu_s'$. The average percent differences of recovered $\mu_a$ and $\mu_s'$ from all phantoms between instruments were 5.9±6.3% and 3.2±3.4% at 681 nm, 5.7±3.3% and 3.4±1.7% at 783 nm, 4.7±5.4% and 3.7±2.9% at 823 nm, 7.4±5.9% and 52±4.1% at 850 nm, respectively. In absolute terms, the average difference in $\mu_a$ was 0.0005 mm$^{-1}$ for $\mu_a$<0.01 mm$^{-1}$, 0.0007 mm$^{-1}$ for 0 01$\mu_a$≤0.015 mm$^{-1}$, and 0.0006 mm$^{-1}$ for $\mu_a$≥0.015 mm–1. Equivalently, the average difference in $\mu_s'$ was 0.03 mm$^{-1}$ for all ranges of $\mu_s'$. These average difference values demonstrate that the mini-FDPM instrument replicates the standard FDPM measurements across a physiologically relevant $\mu_a$ and $\mu_s'$ values.

In all essential characteristics, e.g. signal-to-noise, drift, dynamic range, and noise floor, the mini-FDPM instrument effectively replaces our conventional network-analyzer-based FDPM instrument. In addition, the recovery of optical properties is similar between instruments within about 0.0006 mm$^{-1}$ for $\mu_a$ over the range 0.005 mm$^{-1}$ to 0.022 mm$^{-1}$ and 0.03 mm$^{-1}$ for $\mu_s'$ over the range 0.46 mm$^{-1}$ to 1.5 mm$^{-1}$. Optical property recovery was accomplished 5 times faster, 120 times cheaper, and with equipment over 100 times smaller than with our conventional instrument.

Figure 7:
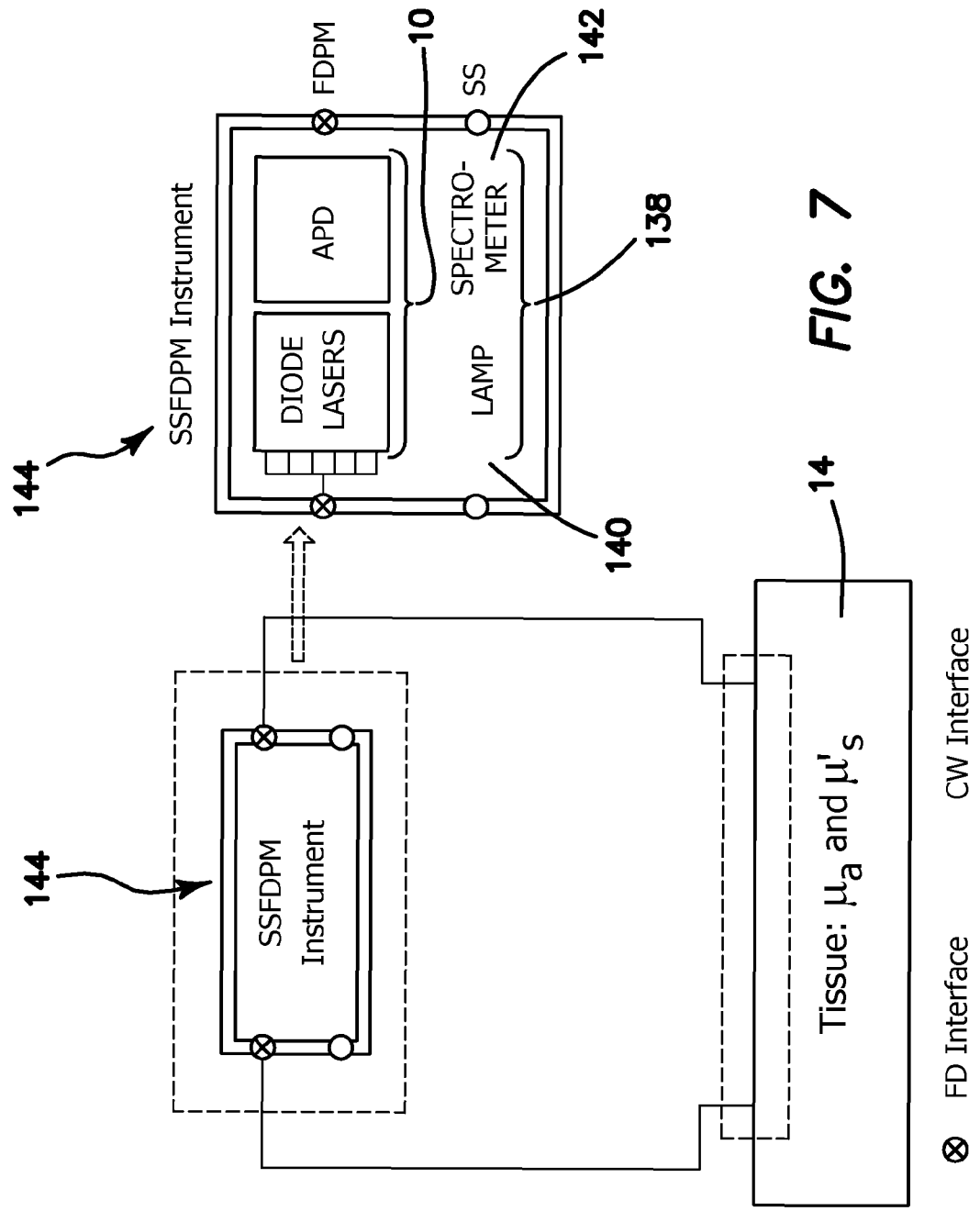
FIG. 7 is a diagram illustrating the combination of the SSFDPM instrument described in connection with FIGS. 1-6 with a steady state broadband spectrometer system.
Figure 8:
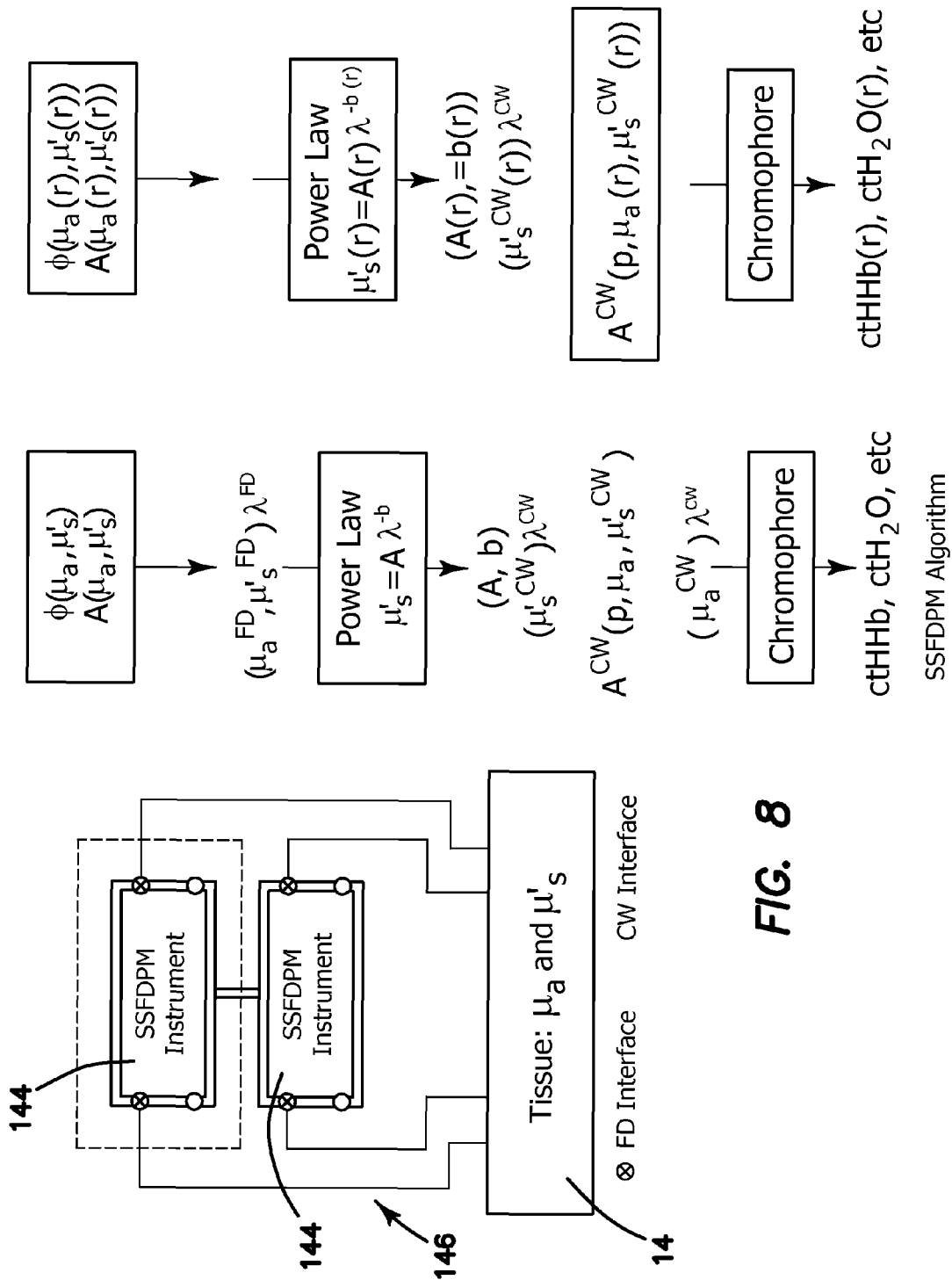
FIG. 8 is a block diagram showing the integration of multiple combined instruments of FIG. 7 into a networked system.
Figure 9:
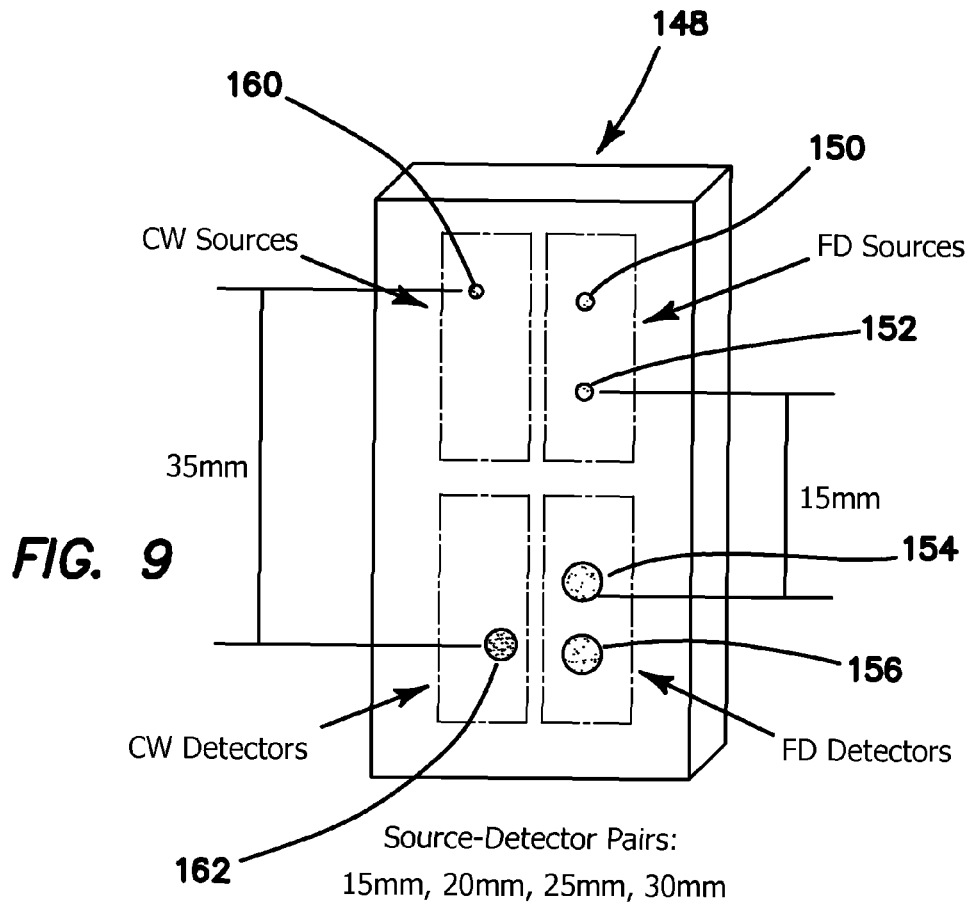
FIG. 9 is a diagram illustrating one embodiment of a measurement head for a fiber optic probe employing a combined instrument of FIG. 7.

The mini-FDPM instrument presented here offers unique opportunities. It currently offers broadband modulation frequency capabilities that are not commercially available. The measurement speed, which is less than 200 ms per wavelength, can be linearly reduced by decreasing the number of modulation frequencies (currently 401). The mini-FDPM instrument may also be combined with a spectrometer system in order to perform spectrally broadband measurements. In this way, the mini-FDPM instrument forms the core of broadband diffuse optical spectroscopy and imaging (DOSI) instruments. The mini-FDPM instrument prototype represents a modular and versatile solution to making broadband FDPM instruments readily available to the research community. The versatility and modularity is first demonstrated by the simple interfacing of the mini-FDPM instrument with any of our handheld probes developed for the standard FDPM instrument. We demonstrated within this disclosure that the mini-FDPM instrument interfaces with the same handheld probe we developed for our clinical breast measurements. Because the mini-FDPM instrument uses standard optical fibers, virtually any multimode fiber-optic probe can interface with the mini-FDPM instrument. The mini-FDPM instrument, offers an expandable solution to increase the number of detection channels and collect spatial information in parallel. The network analyzer is a platform ill suited for practical multichannel clinical diffuse optical imaging. While the parallel collection concept is not novel, parallel detection while retaining broadband information content has not been achieved. By combining the mini-FDPM instrument with a broadband spectrometer system, we envision a spectrally and temporally broadband diffuse optical spectroscopic imaging device 144 that may be configured into many imaging geometries, i.e., handheld probe and tomographic ring. FIG. 7 diagrammatically depicts the combination of FDPM apparatus or instrument 10 combined with a conventional broadband spectrometer system 138 including a broadband continuous wave light source or lamp 140 and a spectrometer 142. The combined instrumentation 144 is used to simultaneously measure tissue 14 with the modulated multiple laser wavelengths and a CW white light. FIG. 8 is a diagram which illustrates the embodiment where multiple broadband diffuse optical spectroscopic imaging devices 144 are integrated into a single system 146 to provide a corresponding multiple of simultaneous temporal and spectral measurements of tissue 14. The outputs of such a multiple devices 144 are coupled or networked to host computer 12 wherein the quantitative broadband absorption and scattering spectroscopy by combined frequency-domain and steady state methodology as disclosed in incorporated U.S. Pat. No. 7,428,434 is simultaneously performed as a function of position in tissue 14. This is symbolically indicated in FIG. 8 by the algorithmic flowchart depictions on the right side of the figure. The arrangement of one embodiment of the head of a fiber optic probe 148 is diagrammed in FIG. 9 where two frequency domain (FD) optic fiber sources 150 and 152 spaced 10 mm apart from each other are place in head 148 so that optic fiber source 152 is spaced 15 mm from the nearest FD fiber optic detector 154, which is another 5 mm distant from FD fiber optic detector 156. In this manner four source-detector pairings are provided for FD measurements with source-detector separations of 15, 20, 25 and 30 mm. Also included in head 148 is the CW white light fiber optic source 160 and CW fiber, optic detector 162 provided with a 35 mm separation.

Many alterations and modifications may be made by those having ordinary skill in the art without departing from the spirit and scope of the embodiments. Therefore, it must be understood that the illustrated embodiment has been set forth only for the purposes of example and that it should not be taken as limiting the embodiments as defined by the following embodiments and its various embodiments.

Therefore, it must be understood that the illustrated embodiment has been set forth only for the purposes of example and that it should not be taken as limiting the embodiments as defined by the following claims. For example, notwithstanding the fact that the elements of a claim are set forth below in a certain combination, it must be expressly understood that the embodiments includes other combinations of fewer, more or different elements, which are disclosed in above even when not initially claimed in such combinations. A teaching that two elements are combined in a claimed combination is further to be understood as also allowing for a claimed combination in which the two elements are not combined with each other, but may be used alone or combined in other combinations. The excision of any disclosed element of the embodiments is explicitly contemplated as within the scope of the embodiments.

The words used in this specification to describe the various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the embodiments.

We claim:

1. A diffuse optical spectroscopic imaging (DOSI) apparatus for spectroscopy in tissue and/or turbid media to measure absorption and scattering properties using multi-frequency frequency domain photon migration in a modular or networkable platform to provide full broadband information content comprising:
    a broadband signal generator;
    a driver having an input coupled to the signal generator;
    a light source coupled to the driver, the light source for exposing the sample to modulated light at one or more wavelengths and one or more modulation frequencies;
    an optical detector comprising a RF switch for selectively switching between RF signals from either internal or external optical subsystems for receiving light from the sample;
    one or more circuits coupled to the optical detector for amplitude and/or phase detection measured by the optical detector;
    a microprocessor gathering the data for amplitude and phase detection from the one or more circuits and communicating with an external host or network computer; and
    a plurality of filters and amplifiers interconnecting the optical detector and amplitude and/or phase detection circuits with each other to isolate signals communicated between the optical detector and amplitude and/or phase detection circuits and increase a signal-to-noise ratio of the signals.

2. The apparatus of claim 1 wherein the broadband signal generator generates a fixed signal and a swept signal in a swept frequency band, and mixes the fixed signal and the swept signal to modulate the light source, which has a modulated optical output in a modulated frequency band.

3. The apparatus of claim 2 where the fixed signal is a fixed 3 GHz signal, where the swept signal is a swept 2.00 to 2.99 GHz broadband signal, and where the modulated optical output is in a 10 MHz to 1 GHz system modulated frequency band.

4. The apparatus of claim 2 where the frequencies of the fixed signal and a swept signal of the broadband signal generator are user selectable.

5. The apparatus of claim 1 where the signal generator comprises a temperature-compensated crystal (TCXO), voltage-controlled (VCO), phase-locked loop (PLL) oscillator generating a precise and stable frequency.

6. The apparatus of claim 1 where the light source comprises one or more light sources at fixed and/or variable wavelengths.

7. The apparatus of claim 6, where the light source comprises four diode lasers at 681, 783, 823, and 850 nm wavelengths and a broadband lamp.

8. The apparatus of claim 1 where the light source further comprises:
    a feedback photodetector optically coupled to the light source; and
    an automatic power control (APC) circuit having a digital potentiometer coupled to the feedback photodetector to compare a monitored current in the light source with a voltage derived from the digital potentiometer to control laser optical power, so that the light source maintains the power constant for optimal performance of the system.

9. The apparatus of claim 1 further comprising an automatic current control (ACC) circuit using precise current monitoring feedback from the driving current.

10. The apparatus of claim 1 where the one or more circuits for amplitude and/or phase detection comprise an up-conversion heterodyne circuit, a down-conversion circuit, an oscillator and a filter, and where the optical detector is connected to the up-conversion heterodyne circuit that generates an intermediate RF signal from the optical detector which is detected using the down-conversion circuit to demodulate the intermediate RF signal by mixing the intermediate RF signal with an oscillating signal from the oscillator, which is filtered by the filter to eliminate crosstalk.

11. The apparatus of claim 10 where the up-conversion heterodyne circuit employs a broadband oscillating signal of 1.955-GHz to 2.945-GHz to generate the up converted intermediate frequency RF signal of 2.955 GHz that is filtered with a high Q dielectric resonator filter and down converted to a low frequency signal at 45 MHz.

12. The apparatus of claim 10 where the up-conversion heterodyne circuit employs a broadband oscillating signal, where the intermediate RF signal, and down conversion frequency of the oscillating signal from the oscillator are user selectable.

13. The apparatus of claim 10 where the down-conversion circuit generates a down converted signal and where the one or more circuits for amplitude and/or phase detection comprise a detector to measure power and phase shift and/or the real and imaginary components of the down converted signal.

14. The apparatus of claim 1 further comprising a multi-port A/D control unit with an integrated fast Ethernet, USB, digital, and/or wireless interface to control the signal generator, driver, light source, optical detector, one or more circuits for amplitude and/or phase detection, and the plurality of filters and amplifiers.

15. The apparatus of claim 1 further comprising a plurality of FDPM apparatus and/or diffuse optical spectroscopic imaging (DOSI) apparatus so that a plurality of FDPM apparatus and/or diffuse optical spectroscopic imaging (DOSI) systems can be networked together to operate as one larger, integrated instrument.

16. The apparatus of claim 1 further comprising a spectrometer system and/or one or more light sources at a plurality of optical wavelengths that are time-independent and/or modulated at frequencies that are lower than those used for light modulation of the apparatus alone.

17. The apparatus of claim 1 where the signal generator modulates the light source at a fixed frequency and/or over a selectable and controllable set of and/or range of frequencies, where the signal generator comprises a fixed frequency oscillator, a variable frequency oscillator and a mixer, wherein an output of the fixed frequency oscillator is mixed with an output of the variable frequency oscillator, the difference between the outputs varying over a range of frequencies and being provided as an output of the mixer to modulate the light source.

18. The apparatus of claim 1 where the signal generator, driver, light source, optical detector, amplitude and/or phase detection circuit are Implemented in modular interconnected boards.

19. The apparatus of claim 1 where the optical detector is adapted for use in measurement of any one of a plurality of tissue types or environments, including, but not limited to breast, brain, bone, joints, muscle, and skin tissues, endoscopic measurements, splanchnic tissues, and/or measurements conducted on any type of optically turbid specimen in any environment, and where the optical detector is placed in contact or proximity with a measured specimen and/or used in conjunction with a light guide and/or lens system to transmit optical signals to the optical detector.

20. A method comprising:
providing data gathered by a microprocessor to an external host or network computer using a diffuse optical spectroscopic imaging (DOSI) apparatus for quantitative spectroscopy as a result of detecting the data using multi-frequency frequency domain photon migration either alone or in combination with time-independent steady state spectroscopy in a modular and/or networkable platform;
generating diffuse optical spectroscopic spectra or images to provide quantitative spectral information content from one or more locations in the measured sample by measuring absorption and scattering properties of tissue or turbid media on the external host or network computer; and
combining the diffuse optical spectroscopic image (DOSI) with a structural and/or functional image to assign and/or co-register DOSI-derived information content to a selected portion of interest in the complementary imaging modality.

21. The method of claim 20 further comprising:
providing a spectrometer system and one or more additional light sources at a plurality of optical wavelengths that are time-independent and/or modulated at frequencies that are lower than that used for light modulation of the diffuse optical spectroscopic imaging (DOSI) apparatus, and
selecting wavelengths of one or more additional light sources using the spectrometer system and/or a combination of switching, dispersion, or temporal/spatial encoding strategies to enhance overall spectral bandwidth and/or spectral information content response at a plurality of optical wavelengths.

* * * * *